(12) United States Patent
Skinner et al.

(10) Patent No.: US 8,114,294 B2
(45) Date of Patent: Feb. 14, 2012

(54) MULTI-LAYERED MACROMOLECULES AND METHODS FOR THEIR USE

(75) Inventors: Charles E. Skinner, Midland, MI (US); William Henry Campbell, Midland, MI (US); Yung K. Kim, Midland, MI (US)

(73) Assignee: Diazem Corporation, Midland, MI (US)

( * ) Notice: Subject to any disclaimer, the term of this patent is extended or adjusted under 35 U.S.C. 154(b) by 887 days.

(21) Appl. No.: 12/151,150

(22) Filed: May 2, 2008

(65) Prior Publication Data

US 2009/0188869 A1    Jul. 30, 2009

Related U.S. Application Data

(62) Division of application No. 11/598,360, filed on Nov. 13, 2006, now Pat. No. 7,384,546.

(51) Int. Cl.
*B01D 15/08* (2006.01)

(52) U.S. Cl. ............ 210/635; 210/656; 210/198.2; 210/502.1; 423/24; 423/25

(58) Field of Classification Search .......... 210/635, 210/656, 198.2, 502.1; 423/24, 25; 428/403, 428/404, 407; 521/25
See application file for complete search history.

(56) References Cited

U.S. PATENT DOCUMENTS

| | | | |
|---|---|---|---|
| 5,530,092 A | 6/1996 | Meijer et al. .......... 528/363 |
| 5,695,882 A | 12/1997 | Rosenberg | |
| 5,739,218 A | 4/1998 | Dvornic et al. | |
| 5,902,863 A | 5/1999 | Dvornic et al. | |
| 5,938,934 A | 8/1999 | Balogh | |
| 5,997,748 A | 12/1999 | Rosenberg | |
| 6,077,500 A | 6/2000 | Dvornic | |
| 6,103,848 A | 8/2000 | Decker et al. .......... 528/21 |
| 6,114,489 A | 9/2000 | Vicari et al. .......... 528/84 |
| 6,288,197 B1 | 9/2001 | Youngs et al. .......... 528/25 |
| 6,288,253 B1 | 9/2001 | Manzer et al. .......... 556/9 |
| 6,307,081 B1 | 10/2001 | Takiuchi et al. .......... 556/434 |
| 6,545,101 B2 | 4/2003 | Agarwal et al. .......... 525/333.7 |
| 6,590,056 B2 | 7/2003 | Won et al. .......... 528/25 |
| 6,599,631 B2 | 7/2003 | Kambe et al. .......... 428/447 |
| 6,794,327 B2 | 9/2004 | Youngs et al. .......... 502/152 |
| 6,803,106 B2 * | 10/2004 | Campbell et al. .......... 428/403 |
| 6,995,215 B2 | 2/2006 | Dvornic et al. .......... 525/474 |
| 7,157,529 B2 * | 1/2007 | Campbell et al. .......... 525/474 |
| 7,384,546 B2 * | 6/2008 | Campbell et al. .......... 210/198.2 |
| 2003/0194555 A1* | 10/2003 | Campbell et al. .......... 428/405 |
| 2004/0224157 A1* | 11/2004 | Campbell et al. .......... 428/405 |
| 2004/0251188 A1* | 12/2004 | Skinner et al. .......... 210/198.2 |
| 2007/0077431 A1* | 4/2007 | Skinner et al. .......... 428/403 |

OTHER PUBLICATIONS

Polymer Preprints, Division of Polymer Chemistry, ACS, vol. 39, No. 1, pp. 473-474, (Mar. 1998).

* cited by examiner

*Primary Examiner* — Ernest G Therkorn
(74) *Attorney, Agent, or Firm* — Robert L. McKellar

(57) ABSTRACT

Multi-layered macromolecules wherein the layers are covalently bonded together and wherein the macromolecules are covalently bonded to solid particulate substrates, methods for the preparation of such compositions, and methods for their uses in a multitude of end use applications ranging from the purification of waste chemical and metal process streams to the separation and identification of proteins, peptides, and oligionucleotides.

2 Claims, 8 Drawing Sheets

P-E + E-P-E-SiO$_2$ $\xrightarrow{\text{HOH}}$ {P-E-O-E}$_{Z'}$-P-{E-SiO$_2$}$_Z$

FIG. 7

Step (B) =   P + E ⟶ P-E

Step (C) =  P-E + SiO$_2$ ⟶ P-E-SiO$_2$

Step (D) =  P-E-SiO$_2$ + E ⟶ E-P-SiO$_2$

Step (F) =  P$_1$ + E ⟶ P$_1$-E

Step (G) =

P$_1$-E + E-P-SiO$_2$ + HOH⟶ P$_1$-E-O-E-P-E-SiO$_2$

Alternative Step =

Step D'   P$_1$+E ⟶ P$_1$E

Step F'   P$_1$-E+E+HOH ⟶ P$_1$-E-O-E

Step G'   P$_1$E-O-E + P-E-SiO$_2$ ⟶ P$_1$-E-O-E-P-E-SiO$_2$

FIG. 8

MULTI-LAYERED MACROMOLECULES AND METHODS FOR THEIR USE

REFERENCE TO RELATED APPLICATIONS

This application is a division of U.S. patent application Ser. No. 11/598,360, filed Nov. 13, 2006, now U.S. Pat. No. 7,384, 546.

This invention deals with multi-layered macromolecules that are chemically bonded to solid particulate substrates, methods for the preparation of such compositions, and methods for their uses in a multitude of end use applications ranging from the purification of waste chemical and metal process streams to the separation and identification of proteins, peptides, and oligionucleotides.

BACKGROUND OF THE INVENTION

Since the decade of the nineteen eighties there has been a large volume of information reported on macromolecules, most specifically, the macromolecules that are dendritic in nature, and those that are hyperbranched.

Dendrimers are described as globular, nano-scale macromolecules consisting of two or more tree-like dendrons, emanating from a single central atom or atomic group called the core. They are comprised of branch cells that are the main building blocks of dendritic structures, that is, three-dimensional analogues of repeat units in classical linear polymers, that must contain at least one branch juncture, and that are organized in mathematically precise architectural arrangements, that give rise to a series of regular radially concentric layers, called generations (G) around the core. Dendrimers must contain at least three different types of branch cells including a core, interior cells, and surface or exterior cells.

Dendrons are the smallest constitutive elements of a dendrimer that have the same architectural arrangement as the dendrimer itself, but which emanate from a single trunk or branch, which may end with a potentially reactive, or a potentially inert functional group called by those skilled in this particular art, the focal group.

On the other hand, hyperbranched polymers are random highly branched macromolecules usually obtained from a "one-shot" polymerization reaction of an $AB_w$ type of monomer, that is $_nAB_w \rightarrow ---(AB_w)_n ---$, where A and B represent mutually reactive functional groups of the monomer. They are usually different from dendrons, in that, hyperbranched macromolecules are considerably more architecturally variable in their structure, have a lower degree of branching, and as materials, usually have a high degree of polydispersity, in that, not all hyperbranched macromolecules of the same hyperbranched polymer are of the same molecular weight or chain length.

A pictorial representation showing in detail the proposed architecture of these types of macromolecular structures can be found in *Polymer Preprints*, Division of Polymer Chemistry, American Chemical Society, Volume 39, Number 1, Pages 473 to 474, (March, 1998).

In addition, much of the detail of these polymers, their chemical reactions schemes, their combinations, and some of their intended and proposed uses can be found in U.S. Pat. No. 5,739,218 that issued to Dvornic, et al. on Apr. 14, 1998; U.S. Pat. No. 5,902,863 that issued to Dvornic, et al. on May 11, 1999; U.S. Pat. No. 5,938,934 that issued to Balogh on Aug. 17, 1999 and U.S. Pat. No. 6,077,500 that issued to Dvornic on Jun. 20, 2000, all of which are incorporated herein by reference for what they teach about the polymers and the methods by which they are made.

Dvornic, et al., in U.S. Pat. Nos. 5,902,863, 5,739,218, and 6,077,500 and Balogh, et al., teach the preparation of organosilicon macromolecules that are based on dendrimer networks that are prepared from radially layered polyamidoamine-organosilicon (PAMAMOS) or polypropyleneimine-organosilicon (PPIOS) dendrimer precursors. The silicon-containing networks have covalently bonded hydrophilic and hydrophobic nanoscopic domains whose size, shape, and relative distribution can be precisely controlled by the reagents and conditions disclosed therein. The PAMAMOS or PPIOS dendrimers can be cross linked into dendrimer-based networks by any number of different types of reactions. For example, Dvornic, et al., in U.S. Pat. No. 5,739,218 teaches hydrophilic dendrimers whose surface has been partially or completely derivatized with inert or functional organosilicon moieties.

Further, Dvornic, et al., in U.S. Pat. No. 6,077,500 teach reacting organosilicon compounds with macromolecules including a higher generation of radially layered copolymeric dendrimers having hydrophilic polyamidoamine or a hydrophilic polypropyleneimine interior and a hydrophobic organosilicon exterior. Balogh et al., teach dendritic polymer based networks that consist of hydrophilic and oleophobic domains.

The general applications for the materials of the above-mentioned patents are for coatings, sensors, sealants, insulators, conductors, absorbents, delivering active species to specific areas such as in catalyst use, drug therapy and gene therapy, personal care uses, and agricultural adjuvant products.

A more recent, somewhat related disclosure utilizing a polyamine as the base polymer can be found in Rosenberg, U.S. Pat. No. 5,695,882 that issued on Dec. 9, 1997 wherein there is disclosed a system for extracting soluble heavy metals from liquid solutions. The process makes use of an activated surface of an extraction material that is a reaction product of an unbranched polyamine with a covalently anchored trifunctional hydrocarbyl silyl that yields non-crosslinked amino groups to which functional chelator groups can be covalently attached. The activated surface of the extraction material is formed by first hydrating the extraction material surface and then silanizing the hydrated surface with a short chain trifunctional silane having a hydrocarbon substituent containing 1 to 6 carbon atoms and a terminal leaving group, and then reacting a polyamine with the hydrocarbysilyl from the silanization of the hydrated surface so as to form an aminohydrocarbyl polymer covalently bound to the extraction material surface. It should be noted that this material is non-crosslinked as is expressly stated therein by the patentees.

A second U.S. patent, namely, U.S. Pat. No. 5,997,748, that issued on Dec. 7, 1999 to Rosenberg and Pang, teaches essentially the same technology as is set forth in the earlier Rosenberg patent as this latter patent is a divisional application from the earlier patent.

What these references do not teach are the inventive compositions, processes for the preparation of the inventive compositions, and the applications for the use of the inventive compositions of this invention as described and claimed herein.

BRIEF DESCRIPTION OF THE DRAWINGS

FIG. 7 is the reaction scheme of the product of FIG. 6 under hydrolysis conditions.

FIG. 8 is a schematic of the reaction sequences of the second process of this invention.

THE INVENTION

Figure 1:
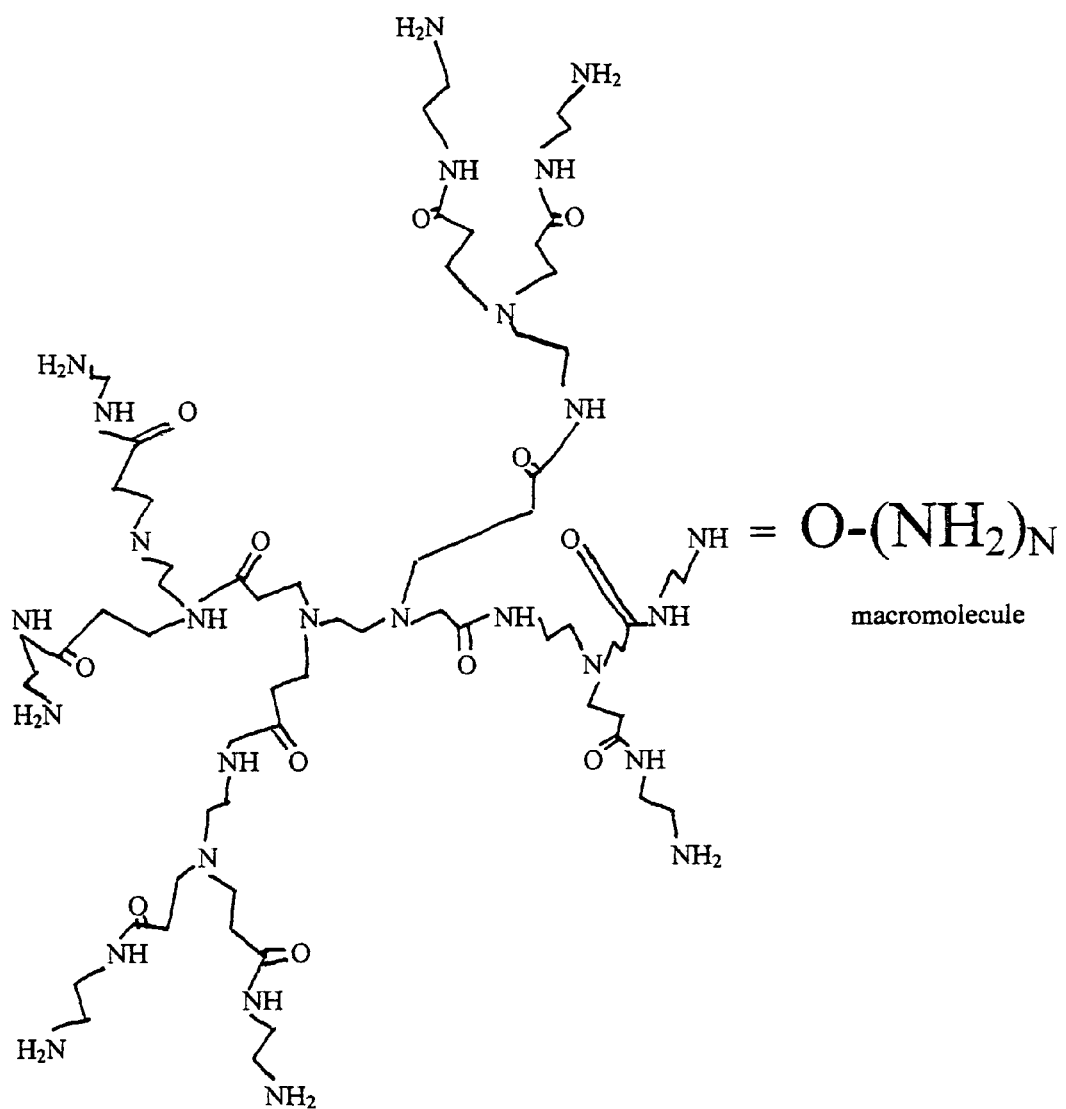
FIG. 1 is an illustration of a base macromolecule.
Figure 2:
FIG. 2 is an illustration of a PANAM repeating unit of FIG. 1.

What is disclosed herein is a first embodiment of this invention that is a multi-layered macromolecule comprising a base macromolecule chemically bonded to a solid particulate substrate wherein the base macromolecule is selected from the group consisting of dendrimers and hyperbranched polymers. The base macromolecule is surmounted by at least one additional layered macromolecule to form at least one chemically bonded layer on the base macromolecule. The layered macromolecule is also selected from the group consisting of dendrimers and hyperbranched polymers.

In another embodiment of this invention there is a process for preparing a multi-layered macromolecule. The process comprises (I) providing a solid particulate substrate capable of reacting with a first lot of a silane bonding agent and (II), contacting the solid particulate substrate with the first lot of silane bonding agent and allowing the solid particulate substrate to react with the first lot of silane bonding agent to form a product.

Then, in step (III), the product thus formed in step (II) is then contacted with a first lot of macromolecule selected from the group consisting of dendrimers and hyperbranched polymers wherein the macromolecule and the product from step (II) are allowed to react with each other. Thereafter, in step (IV), the product from step (III) is contacted with a second lot of silane bonding agent and then the second lot of silane bonding agent and the product from step (III) are allowed to react with each other. In step (V), the process requires providing a second lot of macromolecule and step (VI) provides for contacting the second lot of macromolecule with a third lot of silane bonding agent and allowing the third lot of silane bonding agent and the second lot of base macromolecule to react to form a reactive product.

To finish the process, in step (VII), the product from step (IV) and the product from step (VI) are combined in the presence of water and the product from step (IV) and the product from step (VI) are allowed to react to form a multi-layered macromolecule of this invention.

In yet another embodiment of this invention, there is a second process for preparing a multi-layered macromolecule. The process comprises a first step (A) of providing a first lot of macromolecule selected from the group consisting of dendrimers and hyperbranched polymers. Step (B) provides for contacting the first lot of macromolecule with a first lot of silane bonding agent and allowing the silane bonding agent and the base macromolecule to react with each other.

Step (C) provides for contacting the product from step (B) a with a solid particulate substrate by providing at least one of the conditions selected from the group consisting of (i) initially combining the components in step (C) in the absence of water and thereafter, contacting the combined components with water and, (ii) initially combining the components in step (C) with sufficient water for hydrolysis of any hydrolyzable groups in the components and thereafter, in step (D), adding additional water for crosslinking any silanols formed by the initial water for hydrolysis.

Step (E) provides for treating the product from step (D), after bonding, with a second lot of silane bonding agent and allowing the second lot of silane bonding agent to react with the product from step (D).

The process, in step (F), provides for a second lot of macromolecule and step (G) provides for contacting the second lot of macromolecule with a third lot of silane bonding agent and allowing the second lot of macromolecule and third lot of silane bonding agent to react with each other.

The final step, step (H), provides for combining the product of step (E) and the product of step (G) in the presence of water to form a multi-layered macromolecule.

Still another embodiment of this invention is a process of preparing a multi-layered macromolecule wherein the process comprises (I) providing a macromolecule and reacting the macromolecule with a first lot of silane bonding agent. Step (II) includes providing a second lot of macromolecule and reacting the macromolecule with a second lot of silane bonding agent. A third step involves combining the product from steps (I) and (II) and adding water to co-hydrolyze the silane bonding agents to provide a two layered macromolecule, and then, (III) adding a silane bonding agent and a solid particulate substrate and allowing the components to react to form a multi-layered macromolecule bonded to a solid particulate substrate.

Yet another embodiment of this invention is a process of preparing a multi-layered macromolecule wherein the process comprises (I) providing a solid particulate substrate capable of reacting with a first lot of silane bonding agent and then (II) contacting the solid particulate substrate with a first lot of silane bonding agent and allowing the solid particulate substrate to react with the first lot of silane bonding agent. Thereafter, (III) contacting the product formed in step (II) with a first lot of a macromolecule selected from the group consisting of dendrimers and hyperbranched polymers and allowing the macromolecule and the product from step (II) to react with each other, and then, (IV) providing a second lot of silane bonding agent and a second lot of macromolecule selected from the group consisting of dendrimers and hyperbranched polymers and allowing the second lot of macromolecule and the second lot of silane bonding agent to react with each other. Thereafter, (V) providing a third lot of silane bonding agent and allowing the third lot of silane bonding agent and the product from (IV) to react with each other and thereafter, (VI) contacting the product from (III) and the product from (V) with each other and allowing the product from (III) and the product from (V) to react with each other to form a multi-layered macromolecule.

It should be noted by those skilled in the art that within the scope of this invention, the products of this invention may consist of a dendritic polyamine polymer that can be substituted by a hyperbranched polyamine polymer; a hyperbranched polyamine polymer that can be substituted for a dendritic polyamine polymer; combinations of dendritic polyamine polymers and hyperbranched polyamine polymers can be used; dendritic polyamine polymers can be the first layer of polyamine polymer and a hyperbranched polyamine polymer can be used as the second or multiple layer; a hyperbranched polyamine polymer can be used as the first layer, and a dendritic polyamine polymer can be used as the second or multiple layer, and, finally, the various layers of the polyamine polymers in the products of this invention can be alternated in any combination of layers.

DETAILED DESCRIPTION OF THE INVENTION

Turning now to the details of the present invention and with specificity, there is disclosed herein a composition of matter that is a multi-layered macromolecule that is covalently bonded to a solid particulate substrate.

The basic macromolecules, as the precursor materials of this invention, are based on dendrimers and hyperbranched polymers and FIG. 1 shows an example of one such molecule in which ethylenediamine is the core and the dendrimer is generation 1. The materials are capable of being silicon derivatized to provide the intermediates of this invention, which are further modified by this invention by bonding these materials to a solid particulate substrate and by bonding these materials to each other as layers, upon a base silicon-derivatized macromolecule.

The intermediates of this invention are silicon-derivatized macromolecules that have been derivatized by replacing a portion of the macromolecule's exterior functional sites, such as an amine functionality, with a silane, having additional functional groups. Any macromolecule having an —$NH_2$, OH, COOH, or vinyl groups, or other functional groups that will react with a silane functional group can be silicon-derivatized. They have sizes ranging from about 1 to about 15 nanometers in diameter; molecular weights ranging from about 1,200 to about 1,000,000, for example, and in the dendrimer case, with a hydrophilic PAMAM interior of generation 1, 2, 3 or higher that can be encapsulated in a covalently bonded lyophilic organosilicon outer shell.

The solid particulate substrates of this invention are any particulate mineral materials, including silica, that provide a stable —SiO— bond when bound to a silane bonding agent of this invention. Included in this group are silicas, including fumed, precipitated, and ground silicas, along with other forms, such as silica gels and the like.

Also useful are organic resin particles that have reactive halogens that can react directly with the amine functional polymers described herein, or amine groups that are reactive to the silane bonding agents of this invention, such as Dowex® ion exchange beads, and the like. The silane bonding agents of this invention are any functional silane that comprises a hydrolyzable leaving group that allows the reaction of the silane bonding agent with the solid particulate substrate, or, with silanes with functional groups capable of reacting with the organic resin particles containing a reactive halogen group, and which silanes also contain a reactive group capable of reacting with the functional groups of the macromolecules.

The silane bonding agents of this invention preferably have the general formulae

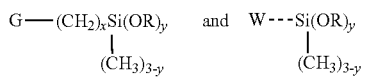

wherein G is selected from the radicals

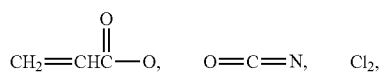

epoxy, and vinyl, and W is selected from $ClCH_2$-Phenyl, and wherein x has a value of from 1 to 6 and y has a value of 1, 2, or 3, R is selected from the group consisting of an alkyl group of from 1 to 6 carbon atoms and the phenyl radical.

The most useful silane bonding agents for this invention are the silane bonding agents having the general formula

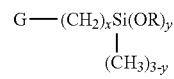

and preferred are those silane bonding agents having the formula:

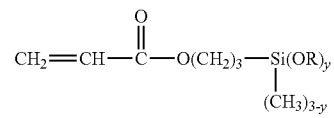

wherein the silane bonding agent

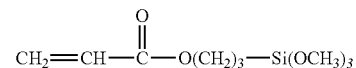

is also one of the most preferred, while the silane bonding agent having the general formula

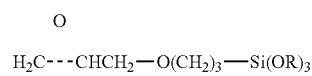

is highly preferred. Most preferred of this general formula is the silane bonding agent

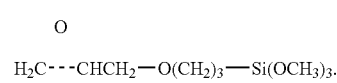

Most preferred of these materials is the aforementioned 3-glycidoxypropyltrimethoxysilane.

Figure 3:
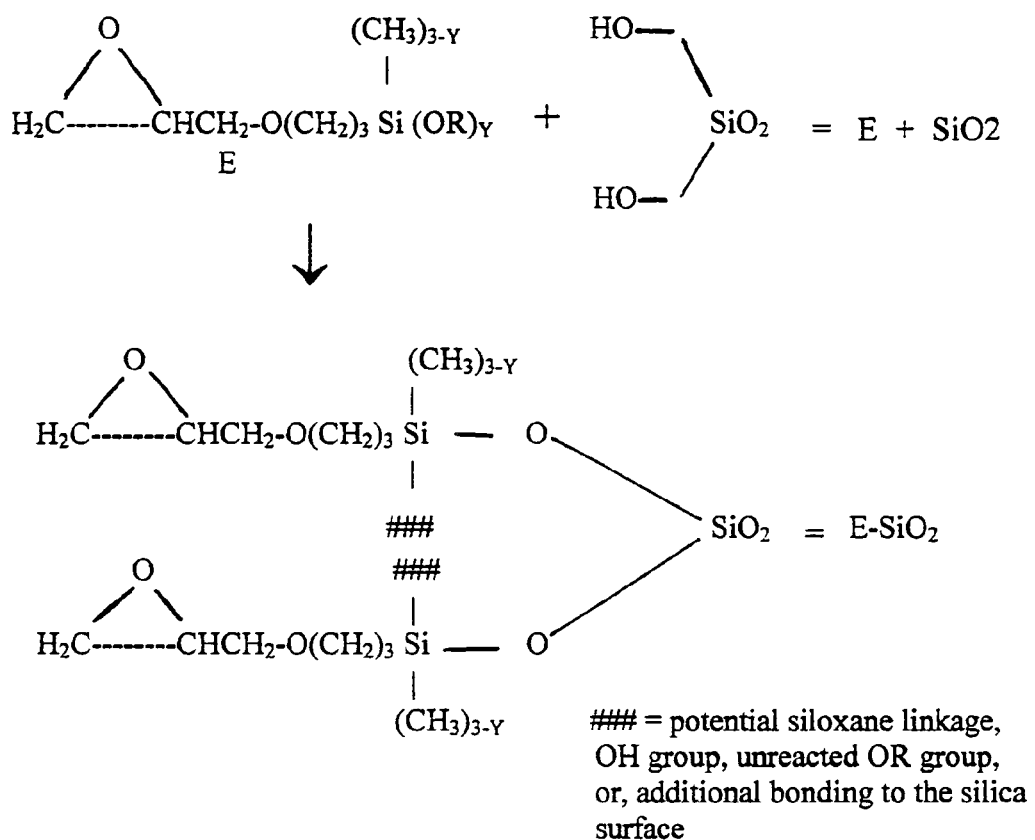
FIG. 3 is an illustration of the reaction scheme of the silane bonding agent with the silica substrate.

By way of example, and with reference to FIG. 3, wherein there is shown a schematic diagram of the incipient stages of the first process of this invention, wherein there is shown step (I), the reaction of the solid particulate substrate depicted as $SiO_2$, and a silane bonding agent depicted as E, wherein the solid particulate substrate is illustrated as silica, and the silane bonding agent is illustrated as a trialkoxy, epoxyalkylene-substituted silane. The reaction in this case gives the product illustrated as E-$SiO_2$ that is the silane bonding agent chemically bonded to the solid silica substrate.

The product E-$SiO_2$ is then reacted with a macromolecule depicted as O—$(NH2)n$ and in this example, it is an amino-functional macromolecule as illustrated in FIG. 1. The schematic representation of the reaction scheme is shown in FIG. 4.

Figure 4:
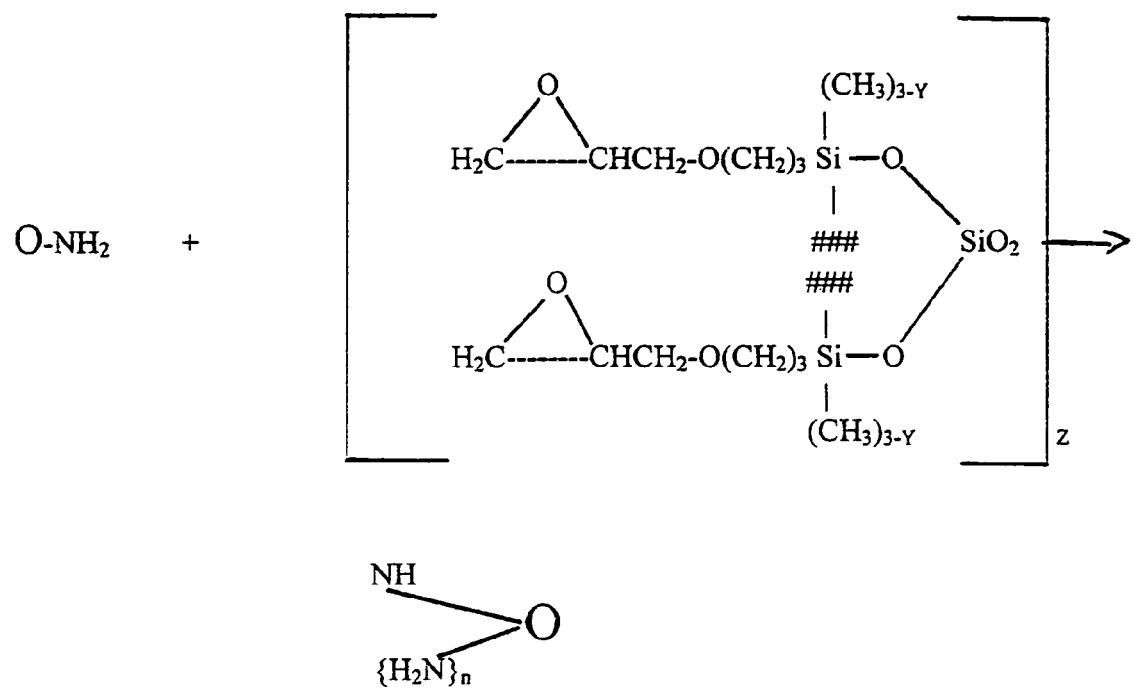
FIG. 4 is the reaction scheme of the product of FIG. 3 and a macromolecule.

Still dealing with the first process of this invention, the product formed by the schematic shown in FIG. 4 is denoted as P-E-$SiO_2$. It should be noted that the value of Z in the formula is the number of amino groups on the amino-functional polymer that have been modified and that the majority of the primary and secondary amine groups on the amino-functional polymer are still unreacted at this point in the process and are therefore still available for further chemical modification. Thus, it should be understood by those in the art that the intent is to use some of the amino groups on the polymer for bonding purposes in this step, but not to completely react every amino group, the reason for which will become apparent from the disclosure, Infra.

At this point in the process, the molecule is a solid particulate substrate indicated by $SiO_2$, having chemically bonded to its surface, the silane bonding agent depicted as E, and an amino functional macromolecule depicted by O—{$NH_2$,}, and is the P-E-$SiO_2$ of the reaction scheme just Supra. This molecule serves as the precursor to the material shown in FIG. 5 that is depicted as E-P-E-$SiO_2$. This chemistry activates the surface of the amino functional polymer for further layering. W is the number of amino groups further modified with the silane bonding agent E.

Still dealing with the first process, the next step is the preparation of an activated amino-functional polymer that can be used to layer the surface of the E-P-E-$SiO_2$ to create the multi-layered composition of this invention.

Figure 6:
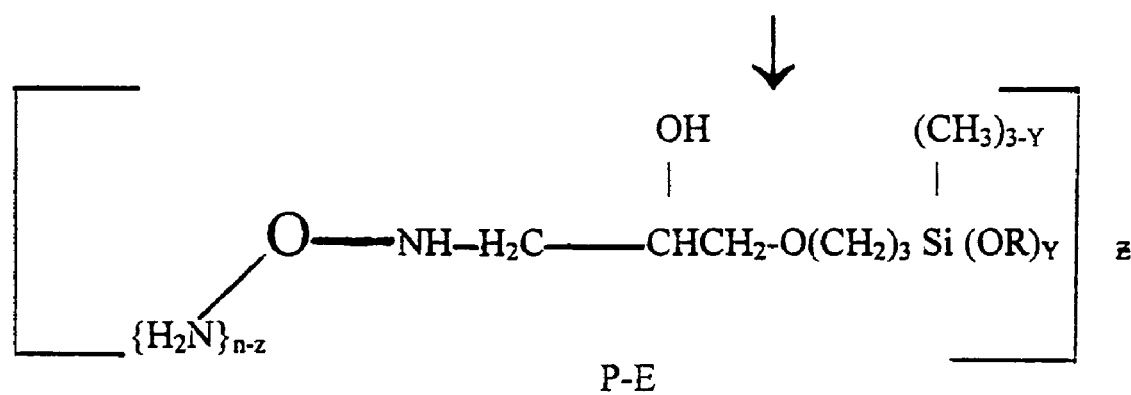
FIG. 6 is the reaction scheme of the product from FIG. 5 and additional polymer.

Thus, with reference to FIG. 6, there is shown schematically, the preparation of the activated amino-functional polymer wherein O—($NH_2$)$_n$ is the amino-functional polymer and E is the silane bonding agent. The epoxyalkylene-substituted trialkoxysilane is shown by way of example.

Figure 5:
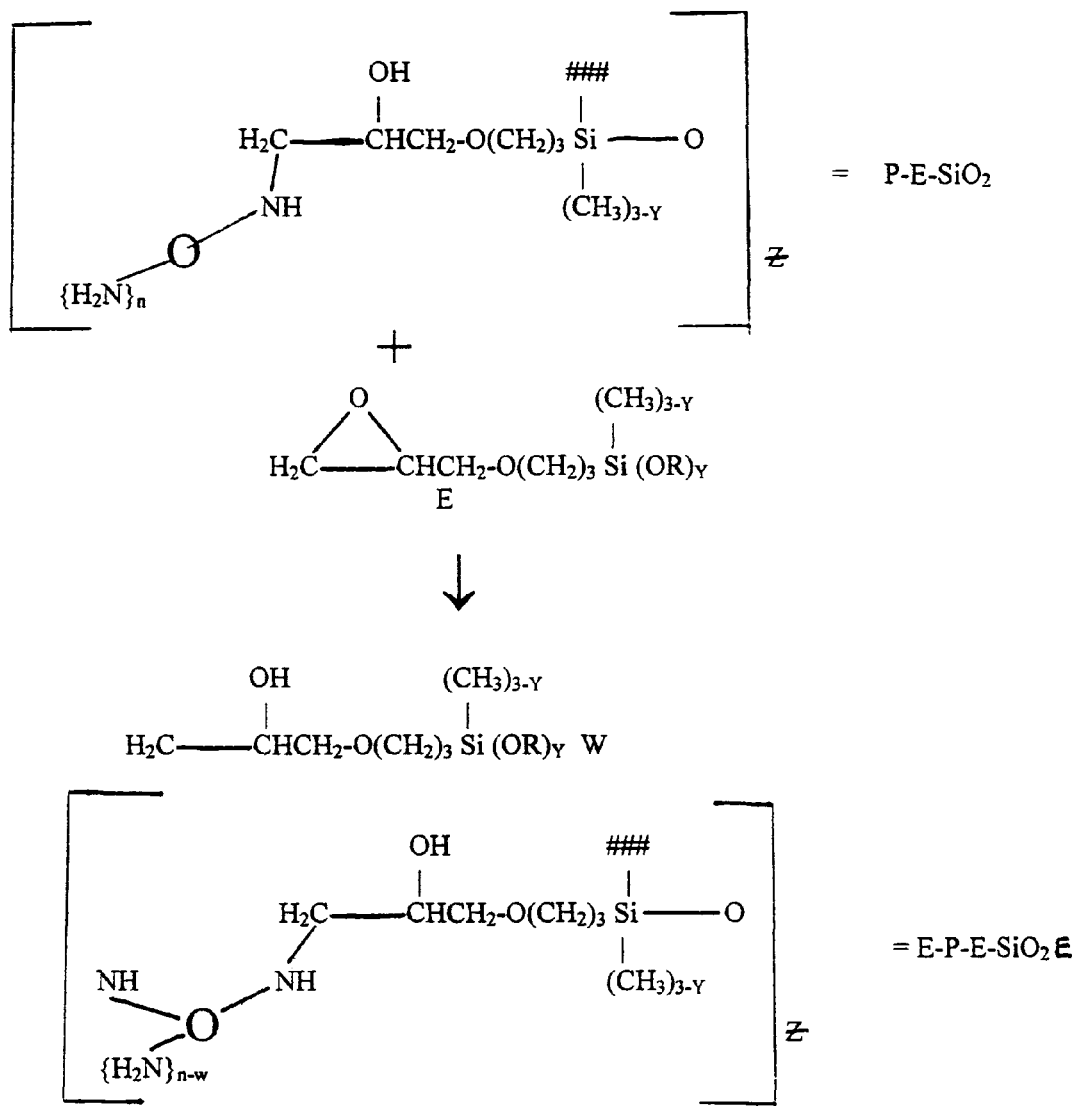
FIG. 5 is the reaction scheme of the product of FIG. 4 and additional silane bonding agent.
Figure 7:
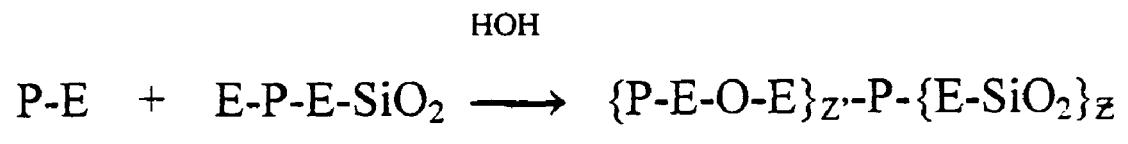

And then finally, FIG. 7 shows the preparation of the multi-layered composition of this invention wherein P-E from FIG. 5 is reacted in the presence of water, with E-P-E-$SiO_2$ from FIG. 6, to give the inventive composition {P-E-O-E}$_Z$-P-{E-$SiO_2$}$_Z$. It should be noted, and it is contemplated within the scope of this invention that additional P-E can be reacted with {P-E-O-E}$_Z$-P-{E-$SiO_2$}$_Z$ to give additional layers of the P-E on the surface thereof. It should be understood by the teachings herein, that each additional layer of P-E that is added to the surface of the polymer provides many additional reactive amino groups for eventual use in the end use applications in which these compositions are contemplated and known by the inventors herein to be useful, many of such end use applications being set forth herein. It is noted for those skilled in the art that this process is the most preferred process for this invention. It was discovered by the inventors herein, that multi-layered compositions of this invention provided capabilities for the end use applications that are not available with known macromolecules, such as those disclosed in the prior art references discussed Supra, among many others.

Turning now to the second process, which is another embodiment of this invention, wherein similar chemistries are used, there is shown in FIG. 8, an illustration of the second process wherein step (A) is the provision of an amino-functional polymer and step (B) is the reaction of the amino-functional polymer (P) with a silane bonding agent (E) which in this example is again illustrated as the epoxyalkylene-substituted trialkoxysilane. Thereafter, the product from step (B) is then (C) reacted with a solid particulate substrate that is, for example, particulate silica that is depicted by $SiO_2$, and then in step (D) the product of step (C) is then reacted with another lot of silane bonding agent as used in step (B). In step (E), a separate lot of amino-functional polymer $P_1$ is provided and in step (F), it is reacted with a separate lot of silane bonding agent to form a reactive amino-functional polymer.

In step (G), the product of step (C) and the product of step (F) are, (i) combined in the presence of water, or in the alternative, (ii) without the presence of water and then after mixing, the combination is subjected to water to provide hydrolysis, and in either alternative, the reaction for coupling the products together takes place to form the product shown as {P-E-O—Si—O-E}$_Z$-P-{E-$SiO_2$}$_Z$. It should be noted that this process is the second most preferred process for this invention.

EXAMPLES

Example 1

A material of this invention was prepared in the following manner. This material is especially useful for chiral separations, metal chelation, complex metal anion capture, and complex acid sequestering.

In a first step, silica, obtained from the PQ Corporation and labeled as MS 3030, having an average particle size of about 90 μm and having a surface area of 320 $m^2$/gm, and having an average pore size of 372 Å, 50 gm. was added to a 0.5 L bottle. Thereafter, 15.7 gm. of 3-glycidoxypropyltrimethoxysilane (Silar Laboratories) was added to achieve a coverage of approximately 2.5 molecules/$nm^2$ on the silica, and the bottle was rolled on a roll mill for about 2 hours. Then, 0.5 gm. of glacial acetic acid was added and the bottle was rolled for 72 hours at room temperature followed by 12 hours of standing at 50° C. The material was washed twice by suspending the product in about 300 millimeters of methanol and then filtered to separate the solids. The material was then re-suspended in about 250 millimeter of methanol and then there was added thereto, 9.9 gms. of water-free polyethyleneimine {BASF, High Molecular Weight (about 24,000)} that had been pre-dissolved in about 100 millimeters of methanol. The mixture was allowed to react within the bottle overnight at room temperature (about 16 hours) and then the bottle was placed in a 40° C. water bath for two hours. The material was washed twice by suspending it in abut 300 millimeters of methanol and then filtering it, then washing it again by suspending in about 300 millimeters of methanol/water mixture of about a 70/30 ratio, and filtering, washing twice again by suspending it in about 300 millimeters of methanol and then filtering. The material was dried at 70° C. for about 16 hours in a convection oven and then sieved through a 150 m sieve to yield about 49.9 gms. (66% yield) of the polymer product.

In step two, 14 gms. of the material from step 1 was re-suspended in 150 millimeters of dimethylformamide and heated to 50° C. and then there was added 0.14 gms. of glacial acetic acid, and the material was allowed to react for 15 minutes. There was then added 0.81 gms. of 3-glydoxypropyldimethylethoxysilane acquired from United Chemical Technologies, and then the material was allowed to react for 72 hours at 50° C.

In step 3, there was added 0.81 gms. of 3-glycidoxypropyldimethylethoxysilane to 150 milliliters of dimethylformamide that had been heated to 50° C. After 15 minutes, there was added 10.8 gms. of high molecular weight polyethyleneimine and it was allowed to react at 50° C. for 72 hours.

In step 4, the material from step 2 was added to the reaction mixture from step 3 and then there was added 0.4 gms. of HPLC grade water and the material was maintained at 50° C. for about 16 hours. The material was then washed twice by suspending it in about 100 milliliters of methanol and then filtering, washing once by suspending it in about 100 milliliters of methanol/water in a 70/30 ratio, followed by oven drying at 70° C. overnight. It was then sieved through a 150 μm sieve to yield 13.6 gms for a 52% yield of the layered polymer.

Example 2

Tests were performed to test the effects of the use of the inventive compositions. Exemplary of the capture of a wide range of metal cations on the layered polymer as prepared in Example 1, is the copper ion capture example discussed Infra.

The copper ion capture capacity of a single layer of the polymer attached on silica of the prior art was compared to silica with two layers of polymer attached to silica provided by example 1, supra.

The comparison was obtained by passing a solution of cupric sulfate acquired from Fisher Chemicals, Certified A.C.S., 0.01M, through a stainless steel column having the dimensions of 250 mm.×4.6 mm., packed by standard liquid chromatography methodology with the double layered material of example 1, having 90 µm particles with an average of 1.2 gms. of media in the column and a second column packed by standard liquid chromatography methodology with the single layered material of the prior art. The cupric sulfate solution was passed through the columns at a flow rate of 1.0 milliliters/minute and the effluent was monitored by UV detection at 790 nm for metal content until breakthrough occurs.

Column breakthrough was observed at 218 milliliters of cupric sulfate solution (0.139 gms. of $Cu^{++}$ or about 11.5 weight percent of the double-layered polymer. Column breakthrough occurred at 60 to 70 milliliters of cupric sulfate solution (0.039 gms. of $Cu^{++}$ or about 3.2 weight percent of the single layered polymer.

For approximately double the amount of the polymer on the surface of the silica, the quantity of copper captured was improved more than three-fold by the double layered polymer.

Example 3

This example deals with the capability of the inventive materials to capture a range of carboxylic acids on the polymer of example 1 using p-aminobenzoic acid (PABA).

The PABA capture of a single layer of polymer bound to silica as provided by the prior art was compared to a material of this invention as provided by Example 1.

The comparison was obtained by passing a solution of p-aminobenzoic acid acquired from the Aldrich Chemical Company, Inc., 99%, 0.04M in 30% methanol and 70% water, through a stainless steel column of 250 mm.×4.6 mm. packed by a standard liquid chromatography methodology with the tethered polymer phase having 90 µm particle with an average of 1.2 gms. of media in the column. The PABA acid solution was passed through the column at a flow rate of 2.0 milliliters/minute and the effluent was monitored by UV detection at 254 nm for the PABA content until breakthrough occurs.

Column breakthrough occurred at 52 milliliters of PABA solution (0.28 gms of PABA or about 23.7 weight percent of the single layer of polymer). For the phase with the double layer of polymer of this invention, the column breakthrough was observed at 90 milliliters of PABA solution (0.49 gms. of PAB or about 41.1 weight percent of the double layer polymer material).

What is claimed is:

1. A method of cleaning copper from a waste stream, the method comprising treating the waste stream using a composition comprising a base macromolecule chemically bonded to a solid particulate substrate wherein the base macromolecule is selected from the group consisting of:
   (a) dendrimers and,
   (b) hyperbranched polymers and,
wherein the base macromolecule is surmounted by at least one chemically bound additional layer of macromolecule to form at least one chemically bonded layer on the base macromolecule, wherein the layered macromolecule is selected from the group consisting of:
   (i) dendrimers and,
   (ii) hyperbranched polymers.

2. A method of recovering copper resources, the method comprising treating a fluid containing said recoverable copper resources with a composition comprising a base macromolecule chemically bonded to a solid particulate substrate wherein the base macromolecule is selected from the group consisting of:
   (a) dendrimers and,
   (b) hyperbranched polymers and,
wherein the base macromolecule is surmounted by at least one chemically bound additional layer of macromolecule to form at least one chemically bonded layer on the base macromolecule, wherein the layered macromolecule is selected from the group consisting of:
   (i) dendrimers and,
   (ii) hyperbranched polymers,
and thereafter, separating the fluid and the composition, and thereafter, recovering the recoverable copper resource from the composition.

* * * * *